US012662442B2

(12) United States Patent
Uy et al.

(10) Patent No.: US 12,662,442 B2
(45) Date of Patent: Jun. 23, 2026

(54) PROCESS FOR PREPARING BISPHENOL A (BPA) IN THE PRESENCE OF AT LEAST TWO IMPURITIES

(71) Applicant: Covestro Deutschland AG, Leverkusen (DE)

(72) Inventors: Jerico Jayson Uy, Antwerp (BE); Erik Sluyts, Brasschaat (BE)

(73) Assignee: Covestro Deutschland AG, Leverkusen (DE)

( * ) Notice: Subject to any disclaimer, the term of this patent is extended or adjusted under 35 U.S.C. 154(b) by 530 days.

(21) Appl. No.: 18/270,651

(22) PCT Filed: Feb. 16, 2022

(86) PCT No.: PCT/EP2022/053774
§ 371 (c)(1),
(2) Date: Jun. 30, 2023

(87) PCT Pub. No.: WO2022/179901
PCT Pub. Date: Sep. 1, 2022

(65) Prior Publication Data
US 2024/0059639 A1 Feb. 22, 2024

(30) Foreign Application Priority Data

Feb. 23, 2021 (EP) ..................................... 21158688

(51) Int. Cl.
C07C 37/20 (2006.01)
C08G 64/24 (2006.01)

(52) U.S. Cl.
CPC .............. C07C 37/20 (2013.01); C08G 64/24 (2013.01)

(58) Field of Classification Search
None
See application file for complete search history.

(56) References Cited

U.S. PATENT DOCUMENTS

| | | | |
|---|---|---|---|
| 4,859,803 A | | 8/1989 | Shaw et al. |
| 5,428,075 A | * | 6/1995 | Pressman ............. B01J 31/0225 |
| | | | 521/26 |
| 2004/0249223 A1 | | 12/2004 | Kumbhar et al. |
| 2004/0249224 A1 | | 12/2004 | Kumbhar et al. |
| 2005/0177006 A1 | | 8/2005 | Neumann et al. |
| 2010/0324341 A1 | | 12/2010 | Terajima et al. |
| 2012/0283485 A1 | * | 11/2012 | Hasyagar ................. B01J 31/10 |
| | | | 521/30 |
| 2014/0051803 A1 | * | 2/2014 | De Brouwer .......... C08G 64/06 |
| | | | 528/196 |
| 2018/0258020 A1 | * | 9/2018 | Nelson .................... C07C 37/74 |

FOREIGN PATENT DOCUMENTS

| | | | |
|---|---|---|---|
| CN | 1872827 A | | 12/2006 |
| TW | 200505833 | | 2/2005 |
| TW | 202030170 | | 8/2020 |
| WO | 2004108640 A2 | | 12/2004 |
| WO | 2012/150560 A1 | | 11/2012 |
| WO | 2020051186 A1 | | 3/2020 |

OTHER PUBLICATIONS

International Search Report for International Patent Application No. PCT/EP2022/053774, mailed May 18, 2022.
Written Opinion for International Patent Application No. PCT/EP2022/053774, mailed May 18, 2022.

* cited by examiner

*Primary Examiner* — Megan McCulley
(74) *Attorney, Agent, or Firm* — K&L Gates LLP

(57) ABSTRACT

The present invention relates to a process for preparing bisphenol A in the presence of at least two impurities being selected from the group consisting of 2-methylbenzofurane, hydroxyacetone, alpha-methylstyrene, acetophenone, benzene and/or cumene without poisoning the catalyst system comprising an ion exchange resin catalyst and a sulfur containing cocatalyst, wherein at least part of the sulfur containing cocatalyst is not chemically bound to the ion exchange resin catalyst. Moreover, the present invention provides a process for preparing polycarbonate.

17 Claims, No Drawings

PROCESS FOR PREPARING BISPHENOL A (BPA) IN THE PRESENCE OF AT LEAST TWO IMPURITIES

CROSS REFERENCE TO RELATED APPLICATIONS

This application is a U.S. national stage application, filed under 35 U.S.C. § 371, of International Application No. PCT/EP2022/053774, which was filed on Feb. 16, 2022, and which claims priority to European Patent Application No. 21158688.8, which was filed on Feb. 23, 2021. The contents of which are hereby incorporated by reference into this specification.

FIELD

The present invention relates to a process for preparing bisphenol A and a process for preparing polycarbonate.

BACKGROUND

Bisphenol A or BPA is an important monomer in the production of polycarbonate or epoxy resins. Normally, BPA is used in the form of para,para-BPA (2,2-Bis(4-hydroxyphenol)propane; p,p-BPA). However, in the production of BPA also ortho, ortho-BPA (o,o-BPA) and/or ortho,para-BPA (o,p-BPA) may be formed. In principle, when referring to BPA, reference is made to para,para-BPA still containing low amounts of ortho, ortho-BPA and/or ortho,para-BPA.

According to the state of the art BPA is produced by reacting phenol with acetone in the presence of an acid catalyst to give the bisphenol. In former times hydrochloric acid (HCl) was used for the commercial process of the condensation reaction. Today, a heterogeneous continuous process for the production of BPA is used in the presence of an ion exchange resin catalyst, wherein said ion exchange resin comprises a crosslinked acid functionalized polystyrene resin. The most important resins are crosslinked polystyrenes with sulfonic acid groups. Divinylbenzene is mostly used as the crosslinking agent as described in GB849965, U.S. Pat. No. 4,427,793, EP0007791 and EP0621252 or Chemistry and properties of crosslinked polymers, edited by Santokh S. Labana, Academic Press, New York 1977.

In order to achieve a high selectivity, the reaction of phenol with acetone can be performed in the presence of suitable co-catalyst. US2005/0177006 A1 and U.S. Pat. No. 4,859,803 describe a process for preparing bisphenol A in the presence of an ion-exchange catalyst and mercaptopropionic acid or a mercaptan as co-catalyst. It is known that the catalyst deactivates over time. For example, the deactivation is described in EPOS 83712, EP10620041, DE14312038. One major objective for the production process is to maximize the performance and dwell times of the catalyst system.

Accordingly, there is a need to identify potential poisonous substances, by-products, impurities of educts etc. in order to deal with this objective.

U.S. Pat. No. 5,414,151 A teaches that improved bisphenol production and an extension in the life of the bisphenol condensation catalyst can be achieved by using as the phenol reactant, a material having less than about 1 ppm of hydroxyacetone. Here the catalyst system comprises an ion exchange resin catalyst and a sulfur containing cocatalyst, wherein the co-catalyst is chemically bound to the ion exchange resin catalyst.

WO2012/150560 A1 teaches the use of a specific catalyst system comprising an ion exchange resin catalyst and a sulfur containing cocatalyst, wherein the co-catalyst is chemically bound to the ion exchange resin catalyst, and also a process for catalyzing condensation reactions between phenols and ketones using such specific catalyst system. Furthermore WO2012/150560 A1 discloses a process for catalyzing condensation reactions between phenols and ketones that does not utilize a bulk promoter that is not chemically bound to the ion exchange resin catalyst.

In the same way EP1520617 A1 describes a process for preparing bisphenols in the presence of an acidic ion-exchange resin catalyst which is modified with specific cationic compound.

U.S. Pat. No. 8,247,619B2 describes the production of BPA based on bio-derived phenol and/or bio-derived acetone in the presence bio-derived impurities in the educts. This document solely describes the use of an ion exchange resin catalyst with attached promotor meaning that the co-catalyst is chemically (i. e. ionically) bound to the ion exchange resin catalyst. 2-Methylbenzofuran (2-MBF or MBF) was found to be a common impurity in fossil fuel-derived but also bio-derived phenol. It was found to react completely during the reaction of phenol and acetone so that no free 2-MBF was detected in the reaction product (BPA). Additionally three new MBF reaction products were observed. Furthermore, the BPA was visually pink and also the polycarbonate prepared using this BPA had a color which was not acceptable. At the same time it was found that not MBF itself was responsible for this color, but the unknown side products of MBF that are obtained during the reaction of phenol and acetone. Those unknowns could not be removed during the BPA purification. Thus, U.S. Pat. No. 8,247,619B2 concludes that the amount of MBF in the bio-derived phenol should be as low as possible in order to obtain low color BPA PC. Catalyst poisoning has not been determined in this prior art document.

Thus, the prior art clearly states that a catalyst system comprising an ion exchange resin catalyst and a chemically bound sulfur containing cocatalyst is prone to hydroxyacetone and/or 2-methyl benzofuran poisoning. Accordingly, the prior art teaches that the concentration of hydroxyacetone and/or 2 methyl benzofuran as impurity in raw phenol and/or raw acetone needs to be reduced as low as possible in order to avoid catalyst poisoning.

Moreover, there are other impurities present in raw acetone and/or raw phenol. For example cumene and/or benzene might be present in raw acetone. Additionally, alpha-methylstyrene, acetophenone and sometimes also cumene might be present in raw phenol. As described above, normally those impurities are tried to be avoided or their amount is reduced as low as possible in order to avoid any side-reactions, poisoning of the catalyst etc. in the desired reaction.

However, the removal of those impurities from raw phenol and/or raw acetone (either fossil based or bio-derived) consumes time and money and thus, renders the raw phenol and/or raw acetone more expensive. In the end it increases the costs of bisphenol A and the respective polymer prepared from this bisphenol A. Moreover, the concentration of different impurities in raw phenol and/or raw acetone varies depending on the supplier and their process of purification of these raw materials. This means that different raw material qualities need to be handled (e. g. another step of purification needs to be performed if the specification exceeds a certain threshold) decreasing flexibility of the process and choice of raw material supplier.

SUMMARY

Therefore, it was an object of the present invention to provide a process for the preparation of ortho,para-, ortho, ortho- and/or para,para-bisphenol A via condensation of phenol and acetone which is more economical than the processes of the prior art. Moreover, it was an object of the present invention to provide a process for the preparation of ortho,para-, ortho, ortho- and/or para,para-bisphenol A via condensation of phenol and acetone which is more flexible and/or which allows more flexibility in the choice of the quality of raw phenol and/or raw acetone. This flexibility should be preferably provided with respect to the concentration of hydroxyacetone, 2-methyl benzofuran, alpha-methylstyrene, benzene, cumene and/or acetophenone as impurity in raw phenol and/or raw acetone.

At least one of the above-mentioned objects, preferably all of these objects have been solved by the present invention. Surprisingly, it has been found that a catalyst system comprising an ion exchange resin catalyst and a sulfur containing cocatalyst, wherein at least part of the sulfur containing cocatalyst is not chemically bound to the ion exchange resin catalyst, is not susceptible to catalyst poisoning by any of the following substances selected from the group consisting of hydroxyacetone, 2-methyl benzofuran, alpha-methylstyrene, benzene, cumene, acetophenone and mixtures thereof. This is surprising, because the prior art suggests that a catalyst system comprising a chemically bound sulfur containing cocatalyst is prone at least to poisoning by hydroxyacetone and/or 2-methyl benzofuran. Moreover, the prior art teaches the necessity to reduce at least the amount of hydroxyacetone and/or 2-methyl benzofuran in raw acetone and/or raw phenol as low as possible. Due to the fact that the specific catalyst system of the present invention is not affected by any of the above-mentioned substances, cheaper raw acetone and/or raw phenol can be used without the risk of reducing catalyst life time. Even two, three, four, five or six selected from the group of substances consisting of hydroxyacetone, 2-methyl benzofuran, alpha-methylstyrene, benzene, cumene and acetophenone can be used at the same time without poisoning of the catalyst system. This renders the overall process more cost effective. In addition, as less energy for purifying the raw materials is needed, the process becomes more ecologically advantageous. Moreover, the process allows more flexibility in the choice of the quality of raw phenol and/or raw acetone, especially with respect to the concentration of at least two substances selected from the group consisting of hydroxyacetone, 2-methyl benzofurane, alpha-methylstyrene, benzene, cumene and acetophenone in those raw materials.

Accordingly, the present invention provides a process for preparing ortho,para-, ortho, ortho- and/or para,para-bisphenol A comprising the step of (a) condensing raw phenol and raw acetone in the presence of a catalyst system, wherein the catalyst system comprises an ion exchange resin catalyst and a sulfur containing cocatalyst, wherein at least part, preferably at least 75 mol-% of the sulfur containing cocatalyst is neither covalently nor ionically bound to the ion exchange resin catalyst at the beginning of process step (a), characterized in that at least two of the following (A) to (F) are true:

(A) the amount of 2-methyl benzofuran present in step (a) is higher than 1 ppm with respect to the total weight of the raw phenol and/or (B) the amount of hydroxyacetone present in step (a) is higher than 1 ppm with respect to the total weight of the sum of the weights of the raw phenol and the raw acetone and/or (C) the amount of alpha-methylstyrene present in step (a) is higher than 1 ppm with respect to the total weight of the raw phenol and/or (D) the amount of acetophenone present in step (a) is higher than 1 ppm with respect to the total weight of the raw phenol and/or (E) the amount of benzene present in step (a) is higher than 1 ppm with respect to the total weight of the raw acetone and/or (F) the amount of cumene present in step (a) is higher than 1 ppm with respect to the total weight of the raw acetone.

DETAILED DESCRIPTION

According to the present invention reference is made to "raw phenol" and/or "raw acetone". The term "raw" is used for the unreacted educts as applied, especially added, in the process for preparing BPA. In particular, this term is used to distinguish the phenol which is freshly added to the reaction (as raw phenol) and the phenol which is recycled in the process for preparing BPA (recycled phenol). Such recycled phenol cannot add additional hydroxyacetone, 2-methyl benzofuran, alpha-methylstyrene and/or acetophenone to the process. The same holds true for acetone which is freshly added to the reaction (as raw acetone) and acetone which is recycled in the process for preparing BPA (recycled acetone). Such recycled acetone cannot add additional hydroxyacetone, cumene and/or benzene. When referring to phenol and/or acetone without any further specification it is preferred that the sum either the chemical compound as such or both raw and recycled phenol and/or raw and recycled acetone are meant.

Hydroxyacetone is an impurity in both raw materials of the reaction of BPA. Raw phenol and raw acetone can both contain hydroxyacetone impurities. Raw phenol can contain 2-methyl benzofuran, alpha-methylstyrene and/or acetophenone. In some cases raw phenol may also contain cumene. Raw acetone can comprise benzene and/or cumene. For example, the production pathways for aceton or phenol are described in Arpe, Hans-Jürgen, Industrielle Organische Chemie, 6. Auflage, Januar 2007, Wiley-VCH. In particular the process for preparing phenol is described in Ullmann's Encyclopedia of Industrial Chemistry, chapters Phenol and Phenol derivatives. The oxidation of cumene, also known as Hock process, is by far the dominant synthetic route to phenol. Among the contaminants formed during the manufacture of phenol are hydroxyketones, especially hydroxyacetone.

The process of the present invention is characterized in that at least two of (A) to (F) are true. According to the present invention, this means that at least any one of the following is met (A)+(B), (A)+(C), (A)+(D), (A)+(E), (A)+(F), (B)+(C), (B)+(D), (B)+(E), (B)+(F), (C)+(D), (C)+(E), (C)+(F), (D)+(E), (D)+(F) or (E)+(F). Preferably, at least three of (A) to (F) are true. This means that at least any one of the following is met (A)+(B)+(C), (A)+(B)+(D), (A)+(B)+(E), (A)+(B)+(F), (A)+(C)+(D), (A)+(C)+(E), (A)+(C)+(F), (A)+(D)+(E), (A)+(D)+(F), (A)+(E)+(F), (B)+(C)+(D), (B)+(C)+(E), (B)+(C)+(F), (B)+(D)+(E), (B)+(D)+(F), (B)+(E)+(F), (C)+(D)+(E), (C)+(D)+(F) or (D)+(E)+(F).

More preferably, the present invention is characterized in that at least (A) and/or (B) is true and that additionally at least one of (C) to (F) is true.

More preferably, at least four of (A) to (F) are true. Even more preferably, at least five of (A) to (F) are true and most preferably (A) to (F) is true. It is understood that in the case where (A) to (F) is true all conditions (A) to (F) are mandatory and all "or"s which connect (A) to (F) need to be deleted (rather the "and"s are mandatory).

In the following reference will be made to each of the possibilities (A) to (F) of which according to the present invention at least two are fulfilled.

According to the present invention "ppm" preferably refers to parts by weight. Moreover, it is understood that any limit given with respect to the amount of any impurity (A) to (F) can be combined with any other limit given with respect to the amount of another impurity (A) to (F).

(A) 2-Methyl Benzofurane

The process of the present invention is characterized in that according to possibility (A) the amount of 2-methyl benzofuran present in step (a) is higher than 1 ppm, preferably higher than 2 ppm, more preferably higher than 3 ppm, still more preferably higher than 4 ppm, still preferably higher than 5 ppm, still more preferably higher than 6 ppm, still more preferably higher than 7 ppm, still more preferably higher than 8 ppm, still more preferably higher than 9 ppm, still more preferably higher than 10 ppm, still more preferably higher than 11 ppm, still more preferably higher than 12 ppm, still more preferably higher than 13 ppm, still more preferably higher than 14 ppm, still more preferably higher than 15 ppm, still more preferably higher than 20 ppm, still more preferably higher than 25 ppm and most preferably higher than 50 ppm with respect to the total weight the raw phenol.

Moreover, it is preferable that for possibility (A) the amount of MBF present in step (a) is higher than 1 ppm and equal to or lower than 5000 ppm, more preferably equal to or lower 4500 ppm, still more preferably equal to or lower 4000 ppm, still more preferably equal to or lower 3500 ppm, still more preferably equal to or lower 3000 ppm, still more preferably equal to or lower 2500 ppm and most preferably equal to or lower 2000 ppm with respect to the total weight of the raw phenol. It is understood that the upper limits given here can be combined with the preferred lower limits given above can be combined. The skilled person knows how to determine the amount of MBF in raw phenol. For example, the amount of 2-methyl benzofuran in raw phenol can be determined according to ASTM D6142-12 (2013).

(B) Hydroxyacetone

According to the present invention it is preferred that for possibility (B) the amount of hydroxyacetone present in step (a) is higher than 1.2 ppm, preferably higher than 1.3 ppm, more preferably higher than 1.4 ppm, still more preferably higher than 1.5 ppm, still preferably higher than 2 ppm, still more preferably higher than 5 ppm, still more preferably higher than 10 ppm and most preferably higher than 50 ppm with respect to the total weight of the sum of the weights of the raw phenol and the raw acetone. Moreover, it is preferable that for possibility (B) the amount of hydroxyacetone present in step (a) is higher than 1.2 ppm and equal to or lower than 5000 ppm, more preferably equal to or lower 4500 ppm, still more preferably equal to or lower 4000 ppm, still more preferably equal to or lower 3500 ppm, still more preferably equal to or lower 3000 ppm, still more preferably equal to or lower 2500 ppm and most preferably equal to or lower 2000 ppm with respect to the total weights of the raw phenol and the raw acetone. It is understood that the upper limits given here can be combined with the preferred lower limits given above can be combined. The skilled person knows how to determine the amount of hydroxyacetone in raw phenol and/or raw acetone. For example, the amount of hydroxyacetone in raw phenol can be determined according to ASTM D6142-12 (2013). The amount of hydroxyacetone in raw acetone can be determined by gas chromatography. For example, formerly the purity of acetone has been determined by ASTM D1154 which is now withdrawn.

(C) alpha-Methylstyrene

The process of the present invention is characterized in that for possibility (C) the amount of alpha-methylstyrene present in step (a) is higher than 1 ppm, preferably higher than 2 ppm, more preferably higher than 3 ppm, still more preferably higher than 4 ppm, still preferably higher than 5 ppm, still more preferably higher than 6 ppm, still more preferably higher than 7 ppm, still more preferably higher than 8 ppm, still more preferably higher than 9 ppm, still more preferably higher than 10 ppm, still more preferably higher than 11 ppm, still more preferably higher than 12 ppm, still more preferably higher than 15 ppm, still more preferably higher than 20 ppm, still more preferably higher than 25 ppm, still more preferably higher than 50 ppm, still more preferably higher than 75 ppm and most preferably higher than 100 ppm with respect to the total weight the raw phenol.

Moreover, it is preferable that the amount of AMS present in step (a) according to possibility (C) is higher than 1 ppm and equal to or lower than 5000 ppm, more preferably equal to or lower 4500 ppm, still more preferably equal to or lower 4000 ppm, still more preferably equal to or lower 3500 ppm, still more preferably equal to or lower 3000 ppm, still more preferably equal to or lower 2500 ppm and most preferably equal to or lower 2000 ppm with respect to the total weight of the raw phenol. It is understood that the upper limits given here can be combined with the preferred lower limits given above. The skilled person knows how to determine the amount of AMS in raw phenol. For example, the amount of AMS in raw phenol can be determined according to ASTM D6142-12 (2013).

(D) Acetophenone

The process of the present invention is characterized in that the amount of acetophenone present in step (a) according to possibility (D) is higher than 1 ppm, preferably higher than 1.5 ppm, more preferably higher than 2 ppm, still more preferably higher than 2.5 ppm, still preferably higher than 3 ppm, still more preferably higher than 4 ppm, still more preferably higher than 5 ppm, still more preferably higher than 6 ppm, still more preferably higher than 7 ppm, still more preferably higher than 8 ppm, still more preferably higher than 9 ppm, still more preferably higher than 10 ppm, still more preferably higher than 11 ppm, still more preferably higher than 12 ppm, still more preferably higher than 13 ppm, still more preferably higher than 15 ppm, still more preferably higher than 20 ppm and most preferably higher than 50 ppm with respect to the total weight the raw phenol.

Moreover, it is preferable that the amount of acetophenone present in step (a) according to possibility (D) is higher than 1 ppm and equal to or lower than 5000 ppm, more preferably equal to or lower 4500 ppm, still more preferably equal to or lower 4000 ppm, still more preferably equal to or lower 3500 ppm, still more preferably equal to or lower 3000 ppm, still more preferably equal to or lower 2500 ppm and most preferably equal to or lower 2000 ppm with respect to the total weight of the raw phenol. It is understood that the upper limits given here can be combined with the preferred lower limits given above can be combined. The skilled person knows how to determine the amount of MBF in raw phenol. For example, the amount of 2-acetophenone in raw phenol can be determined according to ASTM D6142-12 (2013).

(E) Benzene

The process of the present invention is characterized in that the amount of benzene present in step (a) according to possibility (E) is higher than 1 ppm, preferably higher than 2 ppm, more preferably higher than 3 ppm, still more preferably higher than 4 ppm, still preferably higher than 5 ppm, still more preferably higher than 6 ppm, still more preferably higher than 7 ppm, still more preferably higher than 8 ppm, still more preferably higher than 9 ppm, still more preferably higher than 10 ppm, still more preferably higher than 11 ppm, still more preferably higher than 12 ppm, still more preferably higher than 13 ppm, still more preferably higher than 14 ppm, still more preferably higher than 15 ppm, still more preferably higher than 20 ppm, still more preferably higher than 25 ppm, still more preferably higher than 50 ppm, still more preferably higher than 250 ppm and most preferably higher than 300 ppmwith respect to the total weight the raw acetone.

Moreover, it is preferable that the amount of benzene present in step (a) according to possibility (E) is higher than 1 ppm and equal to or lower than 5000 ppm, more preferably equal to or lower 4500 ppm, still more preferably equal to or lower 4000 ppm, still more preferably equal to or lower 3500 ppm, still more preferably equal to or lower 3000 ppm, still more preferably equal to or lower 2500 ppm and most preferably equal to or lower 2000 ppm with respect to the total weight of the raw phenol. It is understood that the upper limits given here can be combined with the preferred lower limits given above. The skilled person knows how to determine the amount of benzene in raw acetone. For example, the amount of benzene in raw acetone can be determined according to ASTM D1154 which is now withdrawn.

(F) Cumene

The process of the present invention is characterized in that the amount of cumene present in step (a) according to possibility (F) is higher than 1 ppm, preferably higher than 2 ppm, more preferably higher than 3 ppm, still more preferably higher than 4 ppm, still preferably higher than 5 ppm, still more preferably higher than 6 ppm, still more preferably higher than 7 ppm, still more preferably higher than 8 ppm, still more preferably higher than 9 ppm, still more preferably higher than 10 ppm, still more preferably higher than 20 ppm, still more preferably higher than 30 ppm, still more preferably higher than 40 ppm, still more preferably higher than 50 ppm, still more preferably higher than 60 ppm, still more preferably higher than 75 ppm, still more preferably higher than 100 ppm, still more preferably higher than 120 ppm, still more preferably higher than 250 ppm and most preferably higher than 300 ppm with respect to the total weight the raw acetone. In one embodiment these amounts refer to the amounts with respect to the total weight of the sum of the weights of the raw phenol and the raw acetone.

Moreover, it is preferable that the amount of cumene present in step (a) according to possibility (F) is higher than 1 ppm and equal to or lower than 5000 ppm, more preferably equal to or lower 4500 ppm, still more preferably equal to or lower 4000 ppm, still more preferably equal to or lower 3500 ppm, still more preferably equal to or lower 3000 ppm, still more preferably equal to or lower 2500 ppm and most preferably equal to or lower 2000 ppm with respect to the total weight of the raw acetone. In one embodiment these amounts refer to the amounts with respect to the total weight of the sum of the weights of the raw phenol and the raw acetone. It is understood that the upper limits given here can be combined with the preferred lower limits given above. The skilled person knows how to determine the amount of cumene in raw acetone. For example, the amount of cumene in raw acetone can be determined according to ASTM D1154 which is now withdrawn.

Preferably the process according to the present invention is characterized in that at least two, preferably at least three, more preferably at least four of the following possibilities (A) to (F) are true:

(A) the amount of 2-methyl benzofuran present in step (a) is higher than 1 ppm and equal to or lower than 5000 ppm, preferably 2000 ppm with respect to the total weight of the raw phenol and/or (B) the amount of hydroxyacetone present in step (a) is higher than 1 ppm and equal to or lower than 5000 ppm, preferably 2000 ppm with respect to the total weight of the sum of the weights of the raw phenol and the raw acetone and/or (C) the amount of alpha-methylstyrene present in step (a) is higher than 1 ppm and equal to or lower than 5000 ppm, preferably 2000 ppm with respect to the total weight of the raw phenol and/or (D) the amount of acetophenone present in step (a) is higher than 1 ppm and equal to or lower than 5000 ppm, preferably 2000 ppm with respect to the total weight of the raw phenol and/or (E) the amount of benzene present in step (a) is higher than 1 ppm and equal to or lower than 5000 ppm, preferably 2000 ppm with respect to the total weight of the raw acetone and/or (F) the amount of cumene present in step (a) is higher than 1 ppm and equal to or lower than 5000 ppm, preferably 2000 ppm with respect to the total weight of the raw acetone.

Preferably the process according to the present invention is characterized in that at least two, preferably at least three, more preferably at least four of the following possibilities (A) to (F) are true:

(A) the amount of 2-methyl benzofuran present in step (a) is higher than 5 ppm, preferably 10 ppm and equal to or lower than 5000 ppm, preferably 2000 ppm with respect to the total weight of the raw phenol and/or (B) the amount of hydroxyacetone present in step (a) is higher than 1.5 ppm, preferably 2 ppm and equal to or lower than 5000 ppm, preferably 2000 ppm with respect to the total weight of the sum of the weights of the raw phenol and the raw acetone (C) the amount of alpha-methylstyrene present in step (a) is higher than 1 ppm, preferably 1.5 ppm and equal to or lower than 5000 ppm, preferably 2000 ppm with respect to the total weight of the raw phenol and/or (D) the amount of acetophenone present in step (a) is higher than 1 ppm, preferably 2 ppm and equal to or lower than 5000 ppm, preferably 2000 ppm with respect to the total weight of the raw phenol and/or (E) the amount of benzene present in step (a) is higher than 2 ppm, preferably 5 ppm and equal to or lower than 5000 ppm, preferably 2000 ppm with respect to the total weight of the raw acetone and/or (F) the amount of cumene present in step (a) is higher than 5 ppm, preferably 10 ppm and equal to or lower than 5000 ppm, preferably 2000 ppm with respect to the total weight of the raw acetone.

Moreover, it is preferred that the process according to the present invention is characterized in that at least one compound of the group consisting of 2-methyl benzofuran, acetophenone, benzene and cumene is present throughout the whole process step (a). It is understood that 2-methyl benzofuran can only be present throughout the whole process step (a), if possibility (B) is true. The same holds true for acetophenone and possibility (D), benzene and possibility (E) and cumene and possibility (F).

According to the present invention it has been found that when using the catalyst system of the present invention, the MBF, acetophenone, benzene and/or cumene if at least one of the possibilities (A), (D), (E) and/or (F) is true does not fully react during process step (a). This means that some of the MBF, acetophenone, benzene and/or cumene is still present in the BPA. Preferably at least 5 wt.-15%, more preferably at least 10 wt.-% and most preferably at least 15 wt.-% with respect to the MBF being present at the beginning of process step (a) are present also at the end of process step (a), preferably at the beginning of process step (b) described below. Preferably at least 5 wt.-%, more preferably at least 10 wt.-% and most preferably at least 15 wt.-% with respect to the MBF being present at the beginning of process step (a) are present in the resulting ortho,para-, ortho, ortho- or para,para-bisphenol A. With respect to MBF it has been found according to the present invention that a side product is formed due to the presence of MBF in reaction step (a). However, not all of the MBF reacts to this impurity. This means that the MBF does not fully react to this impurity. This new side product was analyzed via MS and a molecular weight of 226 g/mol was detected. This suggests an atomic formula of $Ci5H1402$. Therefore, it is preferred that step (a) is conducted in the additional presence of at least one impurity formed due to the presence of MBF in process step (a). Moreover, those impurities can be present in process step (a) in case the phenol fraction of step (b) is recycled in process step (c). Preferably at least 25 wt.-%, more preferably at least 50 wt.-% and most preferably at least 75 wt.-% with respect to the acetophenone being present at the beginning of process step (a) are present also at the end of process step (a), preferably at the beginning of process step (b) described below. Preferably at least 25 wt.-%, more preferably at least 50 wt.-% and most preferably at least 75 wt.-% with respect to the acetophenone being present at the beginning of process step (a) are present in the resulting ortho,para-, ortho, ortho- or para,para-bisphenol A. Preferably at least 20 wt.-%, more preferably at least 40 wt.-% and most preferably at least 60 wt.-% with respect to the benzene being present at the beginning of process step (a) are present also at the end of process step (a), preferably at the beginning of process step (b) described below. Preferably at least 20 wt. %, more preferably at least 40 wt. -% and most preferably at least 60 wt.-% with respect to the cumene being present at the beginning of process step (a) are present also at the end of process step (a), preferably at the beginning of process step (b) described below.

Preferably, the process of the present invention is characterized in that the process additionally comprises the following step:

(b) separating the mixture obtained after step (a) into a bisphenol A fraction comprising at least one of ortho, para-, ortho, ortho- or para,para-bisphenol A and a phenol fraction, wherein the phenol fraction comprises unreacted phenol and at least two substances selected from the group consisting of 2-methyl benzofuran and/or at least one impurity formed due to the presence of 2-methyl benzofuran in step (a), at least one impurity formed due to the presence of hydroxyacetone in step (a), 4-cumylphenol, acetophenone, benzene and cumene.

As has been described above, according to the present invention it has been found that MBF at least partly reacts during process step (a). During step (b) not all of the MBF and/or the impurity formed due to the presence of MBF in step (a) seems to be separated either from the BPA fraction and/or the phenol fraction, especially from the phenol fraction. Accordingly, some of this impurity and/or side product are still present in the phenol fraction. This conclusion holds true also for most of the other impurities depending on which possibility (A) to (F) is true. Furthermore, according to the present invention it has been found that the hydroxyacetone reacts during the process of the present invention and cannot be detected any longer in subsequent process steps. However, at least one new byproduct /impurity seems to be formed due to the presence of hydroxyacetone in step (a). It seems that at least one new impurity is a chromane. This can be present in the phenol fraction of process step (b). Furthermore, has been found according to the present invention that it seems that nearly all of the AMS reacts during process step (a). This has been confirmed, because almost no AMS can be detected after process step (a) (cf. AMS "out" in experimental part). On the other hand it was found that AMS seems to nearly totally react to 4-cumylphenol (only a very small amount of unknowns were detected). Furthermore, additional experiments were conducted that showed that 4-cumylphenol is a stable molecule in process step (a). This means that 4-cumylphenol does not seem to react in process step (a) (cf. the same amount of 4-cumylphenol that was spiked to process step (a) was found at the end of process step (a). Finally, it was found that neither benzene nor cumene react during process step (a). However, at least a small amount of either benzene and/or cumene might be present in the phenol fraction of process step (b).

Preferably, the bisphenol A fraction is taken as product and/or further purified. Several variants of production processes exist to provide the bisphenol of high purity. This high purity is especially of importance for the use of BPA as monomer in the production of polycarbonates. WO-A 0172677 describes crystals of an adduct of a bisphenol and of a phenol and a method for producing these crystals and finally preparing bisphenols. It was found that by crystallizing these adducts a para,para-BPA of high purity can be obtained. EP1944284 describes the process for producing bisphenols wherein the crystallization comprises continuous suspension crystallization devices. It is mentioned that the requirements with respect to the BPA purity are increasing and that with the disclosed method a very pure BPA of higher than 99.7% can be obtained. WO-A 2005075397 describes a process for producing bisphenol A in which the water that is produced during the reaction is removed by distillation. By this method the unreacted acetone is recovered and recycled resulting in an economically favorable process.

Preferably, the process of the present invention is characterized in that the separation in step (b) is performed using a crystallization technique. Still preferably, the separation in step (b) is performed using at least one continuous suspension crystallization device.

It has been further described to make use of a mother liquor cycle. BPA is taken out of the solvent by crystallization and filtration after the reaction. The mother liquor typically contains 5 to 20% BPA and byproducts dissolved in unreacted phenol. Moreover, water is formed during the reaction and is removed from the mother liquor in the dewatering section. Without being bound to a theory, it is believed that at least some of the benzene and/or cumene which has been separated from the BPA will be found in the process water. This means that the benzene and/or cumene is preferably removed from the process of the present invention by dewatering the mother liquor. Such a dewatering can take place for example by using a dewatering column. In the end, the benzene and/or cumene seems to be present in the waste water which can be then treated by a waste water stripper. On the other hand, benzene and/or cumene might also leave the system through the off gases. Moreover, according to the present invention no accumulation of benzene and/or cumene has been observed. This means that indeed the benzene and/or cumene seems to leave the system at some point.

Preferably, the fraction comprising unreacted phenol is recycled for further reaction. This preferably means that the mother liquor is recycled. It is re-used as unreacted phenol in the reaction with acetone in order to give BPA. The flow of mother liquor is preferably conventionally recirculated into the reaction unit.

Typically byproducts in the mother liquor are for example o,p-BPA, o,o-BPA, substituted indenes, hydroxyphenyl indanoles, hydroxyphenyl chromanes, substituted xanthenes and higher condensed compounds. In addition, further secondary compounds such as anisole, mesityl oxide, mesitylene and diacetone alcohol may be formed as a result of self-condensation of the acetone and reaction with impurities in the raw material.

Due to the recycling of mother liquor byproducts accumulate in the circulation stream and can lead to an additional deactivation of the catalyst system. This means for a prolonged use of a catalyst, the impact of initial impurities in the educts have to be considered as well as the impact of possible byproducts in the reaction itself, resulting either from the reaction of phenol with acetone or from a reaction of one of the impurities.

According to the present invention, it is preferred that the process of the present invention is characterized in that the process comprises the additional step of (c) using at least a part of the phenol fraction obtained in step (b) as educt in step (a).

In order to avoid accumulation of the added impurities mentioned in (A) to (F), byproducts and/or impurities formed due to the presence of some of the impurities mentioned in (A) to (F) in step (a) in the system several options exist. Those options include inter alia the purge stream, the waste water, the off gas and the BPA as product itself. One option or maybe also the major one seems to be the purge stream, for example a portion of the mother liquor is discharged. Another approach comprises the passing a part of the entire amount of the circulation stream after solid/liquid separation and before or after the removal of water and residual acetone, over e. g. a rearrangement unit filled with acid ion exchanger. In this rearrangement unit some of the byproducts from BPA preparation are isomerized to give p,p-BPA. It has been found that most of the impurities mentioned in (A) to (F) and/or which are formed due to the presence of MBF, hydroxyacetone and/or alpha-methylstyrene in process step (a) can be removed by a purge stream. Accordingly, it has preferred that at least part of the phenol fraction obtained in step (b) is used as educt in step (a), wherein at least a part of this stream is purged. Preferably, more than 50 vol.-% of the phenol fraction obtained in step (b) is used as educt in step (a), wherein the vol.-% is based on the total volume of the phenol fraction.

Moreover, it was found that some part of the impurity formed due to the presence of alpha-methylstyrene (AMS) in process step (a), preferably the 4-cumylphenol is still present in the resulting BPA using standard techniques to purify the BPA. For example, some of the impurity formed due to the presence of AMS in process step (a), preferably the 4-cumylphenol is still present in the resulting BPA even after performing process step (b) as described above.

The catalyst system which can be used in the process of the present invention is known by the skilled person. Preferably, it is an acidic ion exchange resin. Such ion exchange resin can have from 2% to 20%, preferably 3 to 10% and most preferably 3.5 to 5.5% crosslinkage. The acidic ion exchange resin preferably can be selected from the group consisting of sulfonated styrene divinyl benzene resins, sulfonated styrene resins, phenol formaldehyde sulfonic acid resins and benzene formaldehyde sulfonic acid. Moreover, the ion exchange resin may contain sulfonic acid groups. The catalyst bed can be either a fixed bed or a fluidized bed.

Furthermore, the catalyst system of the present invention comprises a sulfur containing cocatalyst, wherein at least part of the sulfur containing cocatalyst is neither covalently nor ionically bound to the ion exchange resin catalyst. The sulfur containing cocatalyst can be one substance or a mixture of at least two substances. This cocatalyst is preferably dissolved in the reaction solution of process step (a). Still preferably, the cocatalyst is dissolved homogenously in the reaction solution of process step (a). Preferably, the process of the present invention is characterized in that the sulfur containing cocatalyst is selected from the group consisting of mercaptopropionic acid, hydrogen sulfide, alkyl sulfides such as ethyl sulfide and mixtures thereof. Most preferably, the sulfur containing cocatalyst is 3-mercaptopropionic acid.

Preferably, the catalyst system of the present invention comprises a sulfur containing cocatalyst, wherein all of the sulfur containing cocatalyst is neither covalently nor ionically bound to the ion exchange resin catalyst. This means that preferably all of the sulfur containing cocatalyst is added to the process step (a). According to the present invention the expression "not chemically bound" or "neither covalently nor ionically bound" refers to a catalyst system where neither a covalent nor an ionic bound between the ion exchange resin catalyst and the sulfur containing cocatalyst is present at the beginning of process step (a). However, this does not mean that at least part of the sulfur containing cocatalyst might get fixed to the heterogeneous catalyst matrix via ionic or covalent bonds. Nevertheless, at the beginning of process step (a) no such ionic or covalent bonds of the sulfur containing cocatalyst are present, but if they are formed at all, they are formed over time. Accordingly, preferably the sulfur containing cocatalyst is added to process step (a). The term "added" describes an active process step. This means, as said above, that the cocatalyst is preferably dissolved in the reaction solution of process step (a). Additionally the cocatalyst can be added at any other process step or even twice or more times at process step (a). Moreover, preferably, most of the sulfur containing cocatalyst is neither covalently nor ionically bound to the ion exchange resin catalyst. This means that at least 75 mol-%, still preferably at least 80 mol-%, most preferably at least 90 mol-% of the sulfur containing cocatalyst is not chemically bound to the ion exchange resin catalyst. Here the mol-% relate to the total sum of the cocatalyst present in process step (a).

Because MBF, hydroxyacetone, alpha-methylstyrene and/or acetophenone can be impurities in raw phenol, it is preferred that each of the 2-methyl benzofuran, the hydroxyacetone, the alpha-methylstyrene and/or the acetophenone which will be present in step (a) if at least one of (A), (B), (C) and/or (D) is introduced into the process step (a) as impurity in the raw phenol. Nevertheless, at least part of the MBF, hydroxyacetone, alpha-methylstyrene and/or acetophenone can be present in process step (a) due to other reasons. However, it is also possible that cumene is an impurity in raw phenol. Therefore, it is even more preferred that each of the 2-methyl benzofuran, the hydroxyacetone, the alpha-methylstyrene, the cumene and/or the acetophenone which will be present in step (a) if at least one of (A), (B), (C), (D) and/or (F) is fulfilled is introduced into the process step (a) as impurity in the raw phenol. Nevertheless, at least part of the MBF, hydroxyacetone, alpha-methylstyrene, cumene and/or acetophenone can be present in process step (a) due to other reasons.

Because hydroxyacetone, the benzene and/or the cumene can be impurities in raw acetone, it is preferred that each of the hydroxyacetone, benzene and/or cumene which will be present in step (a) if at least one of (B), (E) and/or (F) is fulfilled is introduced into the process step (a) as impurity in the raw acetone. Nevertheless, at least part of the hydroxyacetone, benzene and/or cumene can be present in process step (a) due to other reasons.

In another aspect the present invention provides a process for preparing polycarbonate comprising the steps of (i) obtaining a ortho,para-, ortho, ortho- and/or para,para-bisphenol A according to the process of the present invention in any embodiment or combination of preferred embodiments and (ii) polymerizing the ortho,para-, ortho, ortho- and/or para,para-bisphenol A obtained in step (i), optionally in the presence of at least one further monomer in order to obtain a polycarbonate.

As explained above, the process for the production of ortho,para-, ortho, ortho- and/or para,para-bisphenol A of the present invention provides a BPA which can be obtained in a more economical and/or ecological way. Accordingly, in using this BPA as obtained with the process according to the present invention, the process for preparing polycarbonate according to the present invention is more economical and/or ecological, too.

Reaction step (ii) is known to the skilled person. The polycarbonates can be prepared in a known manner from the BPA, carbonic acid derivatives, optionally chain terminators and optionally branching agents by interphase phosgenation or melt transesterification.

In the interphase phosgenation bisphenols and optionally branching agents are dissolved in aqueous alkaline solution and reacted with a carbonate source, such as phosgene, optionally dissolved in a solvent, in a two-phase mixture comprising an aqueous alkaline solution, an organic solvent and a catalyst, preferably an amine compound. The reaction procedure can also be effected in a plurality of stages. Such processes for the preparation of polycarbonate are known in principle as interfacial processes, for example from H. Schnell, Chemistry and Physics of Polycarbonates, Polymer Reviews, Vol. 9, Interscience Publishers, New York 1964 page 33 et seq., and on Polymer Reviews, Vol. 10, "Condensation Polymers by Interfacial and Solution Methods", Paul W. Morgan, Interscience Publishers, New York 1965, chapter VIII, page 325, and the underlying conditions are therefore familiar to the person skilled in the art.

Alternatively, polycarbonates may also be prepared by the melt transesterification process. The melt transesterification process is described, for example, in Encyclopaedia of Polymer Science, Vol. 10 (1969), Chemistry and Physics of Polycarbonates, Polymer Reviews, H. Schnell, Vol, 9, John Wiley and Sons, Inc. (1964), and DE-C 10 31 512. In the melt transesterification process, the aromatic dihydroxy compounds already described in the case of an interfacial process are transesterified with carbonic acid diesters with the aid of suitable catalysts and optionally further additives in the melt.

Preferably, the process for preparing polycarbonates according to the present invention is characterized in that the process step (i) further comprises a step of purifying the ortho,para-, ortho, ortho- and/or para,para-bisphenol A in order to reduce the amount of at least one compound of the group consisting of 2-methyl benzofuran, an impurity formed due to the presence of hydroxyacetone in step (a), 4-cumylphenol and acetophenone. As has been described above, cheaper raw phenol and/or raw acetone can be used in the process of the present invention. However, when having MBF, hydroxyacetone, AMS and/or acetophenone as impurity in these cheaper raw materials, other impurities are formed and/or the impurities itself seem to remain in the product. These impurities are preferably removed before the polymerization.

EXAMPLES

Materials used in the examples:

| catalyst | acidic polymer-based resin (polystyrene-divinyl-benzene) with sulfonic acid groups, spherical beads, 4% of crosslinking, |
|---|---|
| phenol | Acros Organics, grade: extra pure >99% (measured purity by GC: 99.9%) |
| MEPA | 3-mercaptopropionic acid, Sigma-Aldrich, Purity >99% (measured purity by GC: 99.3%) |
| acetone | VWR, GPR rectapur >99.5% (measured purity by GC: 100%, water not included) |
| hydroxyacetone | Sigma Aldrich, purity 99.0% |
| methanol | Fisher Analytical grade; GC purity 99.99% |
| 2-methyl benzofuran | Sigma Aldrich, purity 99.0% |
| alpha-methylstyrene | Sigma Aldrich M80903 99%, contains 15 ppm p-tert-butylcatechol as inhibitor |
| 4-cumylphenol | Sigma Aldrich 99% Cas No. 599-64-4 |
| acetophenone | Sigma Aldrich >=99.0% Cas Nr 98-86-2 |
| benzene | J T-Baker Analyzed reagent 8014 >99.0% |
| cumene | Sigma Aldrich 98% Cas No. 98-82-8 |

A column reactor was equipped with 150 g of the phenol-wet catalyst (volume of phenol-wet catalyst in the reactor: 210 to 230 ml). The column reactor was heated to 60° C. (catalyst bed temperature during reaction: 63° C.). A mixture of phenol, acetone (3.9 wt.-%) and MEPA (160 ppm with respect to the sum of the masses of phenol and acetone) was prepared and tempered to 60° C. This mixture was pumped into the column reactor with a flow rate of 45 g/h. The column reactor was equipped with a sampling point at the bottom. Using the aperture of the sampling point, different samples were taken during the reaction. Sampling time was 1 h and the amount of the sample taken each hour was 45 g.

A first run (standard run) was conducted for 52 h. After 48 h, 49 h, 50 h and 51h, respectively, a sample was taken and analyzed via GC.

A second run (impurity run) was conducted for 52 h. At the beginning of the second run the respective impurity was dosed to the reaction system (cf. tables for exact amount). After 48 h, 49 h, 50 h and 51h, respectively, a sample was taken and analyzed via GC. After this a fresh mixture of acetone, phenol and MEPA was used and a third run (standard run) was conducted for 52 h. After 48 h, 49 h, 50 h and 51h, respectively, a sample was taken via a syringe and analyzed via GC. Then a fourth run (impurity run) was conducted for 52 h. At the beginning of the fourth run the respective impurity was dosed to the reaction system (cf. tables for exact amount). After 48 h, 49 h, 50 h and 51h, respectively, a sample was taken and analyzed via GC. Finally, a fifth run (standard run) was conducted for 52 h. After 48 h, 49 h, 50 h and 51h, respectively, a sample was taken and analyzed via GC.

The gaschromatography (GC) for methanol was conducted using a column Agilent J&W VF-1MS (100% Dimethylpolysiloxane) of the size 50m×0.25 mm×0.25 μm, a temperature profile of 60° C. for 0.10 min, heating with 12° C./min to 320° C. and holding this temperature for 10.00 min; injecting 1 μl with a split of 10/1 at 300° C.); wherein the flow is 2 ml/min at an initial pressure of 18.3 psi (1.26 bar)

The gaschromatography (GC) for 2-methyl benzofuran, hydroxyacetone, alpha-methyl styrene, acetophenone, benzene, cumene, phenol, para,para BPA were conducted using a column Agilent J&W VF-1MS (100% Dimethylpolysiloxane) of the size 50m×0.25 mm×0.25 μm, a temperature profile of 80° C. for 0.10 min, heating with 12° C./min to 320° C. and holding this temperature for 10.00 min; injecting 1 p.1 with a split of 10/1 at 300° C.); wherein the flow is 2 ml/min at an initial pressure of 18.3 psi (1.26 bar)

The standard run represents the reaction of acetone and phenol in the presence of the catalyst and cocatalyst to form BPA. From this the acetone conversion can be estimated including respective error bars. This conversion represented the baseline to evaluate whether the impurities influence the catalyst deactivation or not. The acetone conversion of standard runs 3 and 5 were compared to the value of standard run 1 to determine the effect of each impurity on the catalyst. If the acetone conversion dropped out of this conversion, it would be proven that the impurity has an effect on the BPA catalyst. In order to show that this kind of evaluation can be used to determine catalyst poisoning, a reference run was conducted using methanol as impurity. It is known from the state of the art that methanol is a known poison for the catalyst in the BPA process that is described for example in US-B 8,143.456. Table 1 shows the respectively obtained results. The values given in the table are the average values obtained from the four samples taken during each run (after 48 h, 49 h, 50 h and 51h).

TABLE 1

| | | reference run with methanol | | | | |
|---|---|---|---|---|---|---|
| Substance | Unit | first run (standard run) | second run (impurity run) | third run (standard run) | fourth run (impurity run) | fifth run (standard run) |
| Acetone conversion | % | 82.63 | 78.65 | 81.92 | 78.20 | 79.42 |
| Methanol IN** | mg/kg | — | 1710 | — | 1660 | — |

**The amount of methanol IN is measured before the catalyst.

As can be clearly seen from table 1, the acetone conversion of each standard run 1, 3 and 5 drops. This means that the catalyst is poisoned by methanol and the conversion cannot be recovered due to irreversible reactions which decrease the catalyst activity.

The following tables show the results of the first run (standard run), the second run (impurity run), the third run (standard run), the fourth run (impurity run) and the fifth run (standard run) for each impurity. The values given in the table are the average values obtained from the four samples taken during each run (after 48 h, 49 h, 50 h and 51h).

TABLE 2

| | | 2-Methyl benzofuran | | | | |
|---|---|---|---|---|---|---|
| Substance | Unit | first run (standard run) | second run (impurity run) | third run (standard run) | fourth run (impurity run) | fifth run (standard run) |
| Acetone conversion | % | 83.53 | 83.27 | 81.54 | 83.72 | 81.47 |
| 2-methyl benzofuran IN** | mg/kg | — | 1590 | | 1580 | |
| 2-methyl benzofuran OUT** | mg/kg | — | 328.50 | | 333.75 | |
| Unknown compound(s) | % | — | 0.22 | — | 0.27 | — |

**The amount of 2-methyl benzofuran IN is measured before the catalyst. The amount of 2-methyl benzofuran OUT is measured from the four samples taken during each run (after 48 h, 49 h, 50 h and 51 h; average value).

As can be seen from the results of table 2, the addition of 2-methyl benzofuran in a reaction of phenol and acetone to para,para-BPA leads to almost no drop in acetone conversion for the standard runs 1, 3 and 5. This means that MBF is no poison for the catalyst system used. This effect can be seen after each impurity run. Moreover, it can be seen that still some MBF is leaving the reactor during the impurity runs (2-methyl benzofuran OUT can be detected). This means that not all of the MBF reacts during the impurity run. The unknow compound(s) was analyzed via GC-MS. The gas chromatography (GC) coupled to mass spectroscopy (MS)

for identification of the unknown compound was performed using a column Agilent J&W VF-1MS (100% Dimethylpolysiloxane) of the size 30m×0.25 mm×0.25 µm, a temperature profile of 60° C. for 0.10 min, heating with 12° C./min 10 to 350° C. and holding this temperature for 5 min; injecting 0.5 µl with a split of 10/1 at 250° C.);

wherein the flow is lml/min at an initial pressure of 24.45 psi (1.685768 bar) and the mass spectrometer scans from mz35— mz 700. At least one unknown compound was found to a molecular weight of 226 g/mol.

TABLE 3

| | | Hydroxy acetone | | | | |
| Substance | Unit | first run (standard run) | second run (impurity run) | third run (standard run) | fourth run (impurity run) | fifth run (standard run) |
| --- | --- | --- | --- | --- | --- | --- |
| Acetone conversion | % | 81.99 | 73.16 | 82.88 | 73.14 | 82.24 |
| Hydroxyacetone IN** | mg/kg | — | 2200 | — | 2200 | — |
| Hydroxyacetone OUT** | mg/kg | — | <5 | — | <5 | — |
| unknown compound(s) | mg/kg | <5 | <5 | <5 | <5 | <5 |

**The amount of hydroxyacetone IN is measured before the catalyst. The amount of hydroxyacetone OUT is measured from the four samples taken during each run (after 48 h, 49 h, 50 h and 51 h; average value).

As can be seen from the results of table 3, the addition of hydroxyacetone in a reaction of phenol and acetone to para,para-BPA leads to no drop in acetone conversion for the standard runs 1, 3 and 5. This means that hydroxyacetone is no poison for the catalyst system used. This effect can be seen after each impurity run. Moreover, it can be seen that nearly all hydroxyacetone reacts during the impurity runs (no hydroxyacetone OUT can be detected). The unknow compound(s) was analyzed via GC-MS. The gas chromatography (GC) coupled to mass spectroscopy (MS) for identification was performed using a column Agilent J&W VF-1MS (100% Dimethylpolysiloxane) of the size 25m×0.2 mm×0.33 µm, a temperature profile of 80° C. for 0.10 min, heating with 10° C./min to 280° C. and holding this temperature for 10.00 min; injecting 1 jt1 with a split of 10/1 at 250° C.); wherein the flow is lml/min at an initial pressure of 24.45 psi (1.685768 bar) and the mass spectrometer scans from mz35— mz 700. Two compounds were found having a molecular weight of 362 g/mol and 434 g/mol.

TABLE 4

| | | Alpha-methylstyrene | | | | |
| Substance | Unit | first run (standard run) | second run (impurity run) | third run (standard run) | fourth run (impurity run) | fifth run (standard run) |
| --- | --- | --- | --- | --- | --- | --- |
| Acetone conversion | % | 82.44 | 83.08 | 84.17 | 81.54 | 83.03 |
| alpha-methylstyrene IN** | mg/kg | — | 1540 | | 1530 | |
| alpha-methylstyrene OUT** | mg/kg | — | <3 | | <3 | |
| 4-cumylphenol | mg/kg | | 2997 | | 3635 | |

**The amount of alpha-methylstyrene IN is measured before the catalyst. The amount of alpha-methylstyrene OUT is measured from the four samples taken during each run (after 48 h, 49 h, 50 h and 51 h; average value).

As can be seen from the results of table 4, the addition of alpha-methylstyrene in a reaction of phenol and acetone to para,para-BPA leads to no drop in acetone conversion for the standard runs 1, 3 and 5. This means that alpha-methylstyrene is no poison for the catalyst system used. This effect can be seen after each impurity run. Moreover, it can be seen that nearly all alpha-methylstyrene reacts during the impurity runs (no alpha-methylstyrene OUT can be detected). By GC analysis it could be proved that alpha-methylstyrene reacted completely to 4-cumylphenol. As 4-cumylphenol is present during the reaction, it can also be concluded that it is no poison for the used catalyst at least in small amounts.

The stability of 4-cumylphenol during the reaction was also tested. This was done using the same set up as described above for alpha-methylstyrene, but dosing 710 ppm 4 cumylphenol. Only one run was performed and at the end the same amount of 4-cumylphenol was detected.

Therefore, it can be concluded that the dosed 4-cumylphenol completely passed through the reactor. Accordingly, 4-cumylphenol is determined to be a stable molecule in the process.

TABLE 5

| | | Acetophenone | | | | |
|---|---|---|---|---|---|---|
| Substance | Unit | first run (standard run) | second run (impurity run) | third run (standard run) | fourth run (impurity run) | fifth run (standard run) |
| Acetone conversion | % | 84.94 | 84.36 | 87.05 | 82.95 | 83.65 |
| Acetophenone IN** | mg/kg | — | 1670 | | 1680 | |
| Acetophenone OUT** | mg/kg | — | 1627 | | 1630 | |

**The amount of acetophenone IN is measured before the catalyst. The amount of acetophenone OUT is measured from the four samples taken during each run (after 48 h, 49 h, 50 h and 51 h; average value).

As can be seen from the results of table 5, the addition of acetophenone in a reaction of phenol and acetone to para,para-BPA leads to almost no drop in acetone conversion for the standard runs 1, 3 and 5. This means that acetophenone is no poison for the catalyst system used. This effect can be seen after each impurity run. Moreover, it can be seen that the acetophenone does not seem to react at all in the system (acetophenone OUT is almost equal to acetophenone IN).

TABLE 6

| | | Benzene | | | | |
|---|---|---|---|---|---|---|
| Substance | Unit | first run (standard run) | second run (impurity run) | third run (standard run) | fourth run (impurity run) | fifth run (standard run) |
| Acetone conversion | % | 82.63 | 81.71 | 83.97 | 81.60 | 83.08 |

After performing the runs, no new unknow compounds were detected by GC. Thus, it seems that all benzene passes the reactor and does not significantly react.

As can be seen from the results of table 6, the addition of benzene in a reaction of phenol and acetone to para,para-BPA leads to almost no drop in acetone conversion for the standard runs 1, 3 and 5. This means that benzene is no poison for the catalyst system used. This effect can be seen after each impurity run. Moreover, it can be concluded that the benzene does not seem to react at all in the system.

TABLE 7

| | | Cumene | | | | |
|---|---|---|---|---|---|---|
| Substance | Unit | first run (standard run) | second run (impurity run) | third run (standard run) | fourth run (impurity run) | fifth run (standard run) |
| Acetone conversion | % | 81.28 | 78.14 | 81.54 | 80.45 | 83.4 |
| Cumene IN** | mg/kg | — | 1820 | | 1790 | |

TABLE 7-continued

| | | Cumene | | | | |
|---|---|---|---|---|---|---|
| Substance | Unit | first run (standard run) | second run (impurity run) | third run (standard run) | fourth run (impurity run) | fifth run (standard run) |
| Cumene OUT** | mg/kg | — | 1815 | | 1800 | |
| | mg/kg | | | | | |

**The amount of cumeneIN is measured before the catalyst. The amount of cumene OUT is measured from the four samples taken during each run (after 48 h, 49 h, 50 h and 51 h; average value).

As can be seen from the results of table 7, the addition of cumene in a reaction of phenol and acetone to para,para-BPA leads to almost no drop in acetone conversion for the standard runs 1, 3 and 5. This means that cumene is no poison for the catalyst system used. This effect can be seen after each impurity run. Moreover, it can be seen that the cumene does not seem to react at all in the system (cumene OUT is almost equal to cumene IN).

Because none of the impurities tested had a substantial effect on the catalyst system, it can be concluded that also the combination of at least two of the tested impurities has a negligible effect on catalyst poisoning.

What is claimed is:

1. A process for preparing ortho,para-, ortho, ortho- and/or para,para-bisphenol A comprising the step of
(a) condensing raw phenol and raw acetone in the presence of a catalyst system, wherein the catalyst system comprises an ion exchange resin catalyst and a sulfur containing cocatalyst, wherein at least part of the sulfur containing cocatalyst is neither covalently nor ionically bound to the ion exchange resin catalyst at the beginning of process step (a),
wherein at least two of the following (A) to (F) are true:
(A) the amount of 2-methyl benzofuran present in step (a) is higher than 1 ppm with respect to the total weight of the raw phenol;
(B) the amount of hydroxyacetone present in step (a) is higher than 1 ppm with respect to the total weight of the sum of the weights of the raw phenol and the raw acetone;
(C) the amount of alpha-methylstyrene present in step (a) is higher than 1 ppm with respect to the total weight of the raw phenol;
(D) the amount of acetophenone present in step (a) is higher than 1 ppm with respect to the total weight of the raw phenol;
(E) the amount of benzene present in step (a) is higher than 1 ppm with respect to the total weight of the raw acetone;
(F) the amount of cumene present in step (a) is higher than 1 ppm with respect to the total weight of the raw acetone.

2. The process according to claim 1, wherein at least two of the following (A) to (F) are true:
(A) the amount of 2-methyl benzofuran present in step (a) is higher than 1 ppm and equal to or lower than 5000 ppm, with respect to the total weight of the raw phenol;
(B) the amount of hydroxyacetone present in step (a) is higher than 1 ppm and equal to or lower than 5000 ppm, with respect to the total weight of the sum of the weights of the raw phenol and the raw acetone;
(C) the amount of alpha-methylstyrene present in step (a) is higher than 1 ppm and equal to or lower than 5000 ppm, with respect to the total weight of the raw phenol;

(D) the amount of acetophenone present in step (a) is higher than 1 ppm and equal to or lower than 5000 ppm, with respect to the total weight of the raw phenol;
(E) the amount of benzene present in step (a) is higher than 1 ppm and equal to or lower than 5000 ppm, with respect to the total weight of the raw acetone; and/or
(F) the amount of cumene present in step (a) is higher than 1 ppm and equal to or lower than 5000 ppm, with respect to the total weight of the raw acetone.

3. The process according to claim 1, wherein at least two of the following (A) to (F) are true:
(A) the amount of 2-methyl benzofuran present in step (a) is higher than 10 ppm and equal to or lower than 5000 ppm, with respect to the total weight of the raw phenol;
(B) the amount of hydroxyacetone present in step (a) is higher than 1.5 ppm and equal to or lower than 5000 ppm, with respect to the total weight of the sum of the weights of the raw phenol and the raw acetone;
(C) the amount of alpha-methylstyrene present in step (a) is higher than 1 ppm and equal to or lower than 5000 ppm, with respect to the total weight of the raw phenol;
(D) the amount of acetophenone present in step (a) is higher than 1 ppm and equal to or lower than 5000 ppm, with respect to the total weight of the raw phenol;
(E) the amount of benzene present in step (a) is higher than 2 ppm and equal to or lower than 5000 ppm, with respect to the total weight of the raw acetone; and/or
(F) the amount of cumene present in step (a) is higher than 10 ppm and equal to or lower than 5000 ppm, with respect to the total weight of the raw acetone.

4. The process according to claim 1, wherein at least one compound of the group consisting of 2-methyl benzofuran, acetophenone, benzene and cumene is present throughout the whole process of step (a).

5. The process according to claim 1, wherein the process further comprises the following step:
(b) separating the mixture obtained after step (a) into a bisphenol A fraction comprising at least one of ortho, para-, ortho, ortho- or para,para-bisphenol A and a phenol fraction, wherein the phenol fraction comprises unreacted phenol and at least two substances selected from the group consisting of 2-methyl benzofuran and/or at least one impurity formed due to the presence of 2-methyl benzofuran in step (a), at least one impurity formed due to the presence of hydroxyacetone in step (a), 4-cumylphenol, acetophenone, benzene and cumene.

6. The process according to claim 5, wherein the separation in step (b) is performed using a crystallization technique.

7. The process according to claim 5, wherein the process further comprises the additional step of
(c) using at least a part of the phenol fraction obtained in step (b) as educt in step (a).

8. The process according to claim 1, wherein the sulfur containing cocatalyst is selected from the group consisting of mercaptopropionic acid, hydrogen sulfide, alkyl sulfides and mixtures thereof.

9. The process according to claim 8, wherein the alkyl sulfide is ethyl sulfide.

10. The process according to claim 1, wherein each of the 2-methyl benzofuran, the hydroxyacetone, the alpha-methylstyrene, the acetophenone and/or the cumene which will be present in step (a) if at least one of (A), (B), (C), (D) and/or (F) is fulfilled is introduced into the process of step (a) as impurity in the raw phenol.

11. The process according to claim 1, wherein each of the hydroxyacetone, the benzene and/or the cumene which will be present in step (a) if at least one of (B), (E) and/or (F) is fulfilled is introduced into the process of step (a) as impurity in the raw acetone.

12. A process for preparing polycarbonate comprising the steps of (i) obtaining a ortho,para-, ortho, ortho- and/or para,para-bisphenol A according to the process of claim 1 and (ii) polymerizing the ortho,para-, ortho,ortho- and/or para, para-bisphenol A obtained in step (i).

13. The process according to claim 12, wherein the process of step (i) further comprises a step of purifying the ortho, para-, ortho, ortho- and/or para, para-bisphenol A in order to reduce the amount of at least one compound of the group consisting of 2-methyl benzofuran, an impurity formed due to the presence of hydroxyacetone in step (a), 4-cumylphenol and acetophenone.

14. The process of claim 12, wherein step (ii) is performed in the presence of at least one further monomer in order to obtain a polycarbonate.

15. The process of claim 1, wherein at least 75 mol % of the sulfur containing cocatalyst of the catalyst system of step (a) is neither covalently nor ionically bound to the ion exchange resin catalyst at the beginning of process step (a).

16. The process according to claim 1, wherein at least two of the following (A) to (F) are true:

(A) the amount of 2-methyl benzofuran present in step (a) is higher than 1 ppm and equal to or lower than 2000 ppm, with respect to the total weight of the raw phenol;

(B) the amount of hydroxyacetone present in step (a) is higher than 1 ppm and equal to or lower than 2000 ppm, with respect to the total weight of the sum of the weights of the raw phenol and the raw acetone;

(C) the amount of alpha-methylstyrene present in step (a) is higher than 1 ppm and equal to or lower than 2000 ppm, with respect to the total weight of the raw phenol;

(D) the amount of acetophenone present in step (a) is higher than 1 ppm and equal to or lower than 2000 ppm, with respect to the total weight of the raw phenol;

(E) the amount of benzene present in step (a) is higher than 1 ppm and equal to or lower than 2000 ppm, with respect to the total weight of the raw acetone; and/or (F) the amount of cumene present in step (a) is higher than 1 ppm and equal to or lower than 2000 ppm, with respect to the total weight of the raw acetone.

17. The process according to claim 1, wherein at least two of the following (A) to (F) are true:

(A) the amount of 2-methyl benzofuran present in step (a) is higher than 10 ppm and equal to or lower than 2000 ppm, with respect to the total weight of the raw phenol;

(B) the amount of hydroxyacetone present in step (a) is higher than 1.5 ppm and equal to or lower than 2000 ppm, with respect to the total weight of the sum of the weights of the raw phenol and the raw acetone;

(C) the amount of alpha-methylstyrene present in step (a) is higher than 1 ppm and equal to or lower than 2000 ppm, with respect to the total weight of the raw phenol;

(D) the amount of acetophenone present in step (a) is higher than 1 ppm and equal to or lower than 2000 ppm, with respect to the total weight of the raw phenol;

(E) the amount of benzene present in step (a) is higher than 2 ppm and equal to or lower than 2000 ppm, with respect to the total weight of the raw acetone; and/or (F) the amount of cumene present in step (a) is higher than 10 ppm and equal to or lower than 2000 ppm, with respect to the total weight of the raw acetone.

* * * * *